US008795264B2

(12) United States Patent
Zipper

(10) Patent No.: US 8,795,264 B2
(45) Date of Patent: *Aug. 5, 2014

(54) METHOD FOR DECREASING THE SIZE AND/OR CHANGING THE SHAPE OF PELVIC TISSUES

(76) Inventor: Ralph Zipper, Melbourne, FL (US)

( * ) Notice: Subject to any disclaimer, the term of this patent is extended or adjusted under 35 U.S.C. 154(b) by 938 days.

This patent is subject to a terminal disclaimer.

(21) Appl. No.: 12/496,216

(22) Filed: Jul. 1, 2009

(65) Prior Publication Data

US 2010/0004644 A1 Jan. 7, 2010

Related U.S. Application Data

(60) Provisional application No. 61/077,348, filed on Jul. 1, 2008.

(51) Int. Cl.
*A61B 18/18* (2006.01)

(52) U.S. Cl.
USPC .................................. 606/14; 606/13; 606/15

(58) Field of Classification Search
CPC ....... A61B 18/201; A61B 18/24; A61B 18/20
USPC .......................................................... 606/14
See application file for complete search history.

(56) References Cited

U.S. PATENT DOCUMENTS

| 4,862,886 A | 9/1989 | Clarke et al. |
|---|---|---|
| 5,219,343 A | 6/1993 | L'Esperance, Jr. |
| 5,458,596 A | 10/1995 | Lax et al. |
| 5,569,242 A | 10/1996 | Lax et al. |
| 5,649,973 A | 7/1997 | Tierney et al. |
| 5,725,522 A | 3/1998 | Sinofsky |
| 5,863,531 A | 1/1999 | Naughton et al. |
| 5,919,219 A * | 7/1999 | Knowlton ..................... 607/102 |
| 5,948,011 A | 9/1999 | Knowlton |
| 5,957,920 A | 9/1999 | Baker |
| 6,156,032 A * | 12/2000 | Lennox .......................... 606/41 |

(Continued)

FOREIGN PATENT DOCUMENTS

WO WO9304727 3/1993

OTHER PUBLICATIONS

Pendergrass, P.B. et al., Surface Area of the Human Vagina as Measured from Vinyl Polysiloxane Casts, 2003, Gynecologic and Obstetric Investigation, 55, 110-113.*

(Continued)

*Primary Examiner* — Gary Jackson
*Assistant Examiner* — John R Downey
(74) *Attorney, Agent, or Firm* — Stephen C. Thomas

(57) ABSTRACT

Methods for decreasing the size and/or changing the shape of pelvic tissues. Energy, preferably radio frequency or laser energy, may be applied to endopelvic fascia or other subcutaneous tissue transcutaneously, through one or more incisions in skin, or directly to the desired subcutaneous tissue after a strip of mucosa or skin has been removed. Such an application of energy may cause the subcutaneous tissue to shrink, thereby bringing the mucosa or skin edges closer together while minimizing damage to deep nerves and other surrounding tissues. Such manipulation of the layers of the skin may be utilized to decrease the size or change the shape of numerous anatomical structures and may also serve to alleviate the symptoms of urinary incontinence, dyspareunia, or chronic pelvic pain. The method steps of the present invention may further provide for the beneficial pretreatment of a tissue site prior to stem cell implantation.

17 Claims, 9 Drawing Sheets

(56) References Cited

U.S. PATENT DOCUMENTS

| | | | |
|---|---|---|---|
| 6,216,704 B1 | 4/2001 | Ingle et al. | |
| 6,292,700 B1 | 9/2001 | Morrison et al. | |
| 6,387,088 B1 | 5/2002 | Shattuck et al. | |
| 6,463,331 B1 * | 10/2002 | Edwards | 607/101 |
| 6,587,731 B1 | 7/2003 | Ingle et al. | |
| 6,607,525 B2 | 8/2003 | Franco | |
| 7,049,057 B2 | 5/2006 | Atala et al. | |
| 7,315,762 B2 | 1/2008 | Mosher et al. | |
| 2003/0065400 A1 | 4/2003 | Beam et al. | |
| 2003/0096407 A1 | 5/2003 | Atala et al. | |
| 2003/0232303 A1 | 12/2003 | Black | |
| 2007/0082403 A1 | 4/2007 | Yang et al. | |
| 2007/0190544 A1 | 8/2007 | Giannakakou et al. | |
| 2007/0233191 A1 | 10/2007 | Parmer | |
| 2008/0125771 A1 * | 5/2008 | Lau et al. | 606/41 |
| 2008/0195087 A1 | 8/2008 | Wang et al. | |
| 2008/0201826 A1 | 8/2008 | Pryor et al. | |
| 2008/0262394 A1 | 10/2008 | Pryor et al. | |
| 2008/0269205 A1 * | 10/2008 | Loebel et al. | 514/226.2 |
| 2008/0306472 A1 | 12/2008 | Pryor et al. | |
| 2009/0012587 A1 | 1/2009 | Wang et al. | |
| 2009/0054883 A1 * | 2/2009 | Stolen et al. | 606/14 |
| 2009/0082759 A1 | 3/2009 | Pryor et al. | |
| 2009/0153837 A1 | 6/2009 | Wang et al. | |
| 2009/0299236 A1 | 12/2009 | Pryor et al. | |
| 2009/0319008 A1 * | 12/2009 | Mayer | 607/90 |
| 2010/0241038 A1 | 9/2010 | Pryor et al. | |
| 2010/0256541 A1 | 10/2010 | Pryor et al. | |
| 2010/0286576 A1 | 11/2010 | Pryor et al. | |
| 2011/0000420 A1 | 1/2011 | Vaught | |
| 2011/0004202 A1 | 1/2011 | Zipper | |
| 2011/0004203 A1 | 1/2011 | Zipper | |
| 2011/0009852 A1 | 1/2011 | Pryor et al. | |
| 2011/0020173 A1 | 1/2011 | Pryor et al. | |
| 2011/0144724 A1 | 6/2011 | Pryor et al. | |
| 2011/0144725 A1 | 6/2011 | Pryor et al. | |
| 2011/0144726 A1 | 6/2011 | Pryor et al. | |
| 2011/0224584 A1 | 9/2011 | Pryor et al. | |

OTHER PUBLICATIONS

Birken LVR of the Woodlands, http://www.lvrofthewoodlandstx.com/birken_blog/[Mar. 3, 2009 8:34:04 AM].

Dr. David Matlock, MD, The Aesthetic Guide Primary Care Edition Autumn 2008, www.miinews.com.

Medical Diode Laser 15-30W 810/980nm , http://www.tradekey.com/product_view/id/469128.htm [Mar. 3, 2009 8:39:26 AM].

Office Action on U.S. Appl. No. 12/687,965 dated Mar. 13, 2013 for applicant Ralph Zipper.

Journal of the Laser and Health Academy, vol. 2012, No. 1; www.laserandhealth.com, May 2012.

* cited by examiner

METHOD FOR DECREASING THE SIZE AND/OR CHANGING THE SHAPE OF PELVIC TISSUES

CROSS REFERENCE TO RELATED APPLICATIONS

This application claims the benefit of provisional patent application Ser. No. 61/077,348, filed with the USPTO on Jul. 1, 2008, which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention generally relates to surgical methods, more specifically, the present invention relates to changing the shape and/or size of tissues and structures within the pelvic region including but not limited to the vagina, labia, prepuce, perineum, and other tissues.

2. Background Art

Many women are unhappy with the size, shape, and/or contour of the vagina or labia. This may be secondary to changes that occur with childbirth, vaginal or pelvic surgery, and/or aging. Sometimes the size, shape, and/or contour abnormality may be congenital. This enlargement and/or unsatisfactory shape or contour may lead to sexual dysfunction which may be anatomic or psychological in nature. Until recently, vaginal reconstruction and vulvar surgery has been reserved for the treatment of neoplasia and prolapse. As women have become more outspoken about their dissatisfaction with their genitalia, surgeons have begun to offer those patients surgical corrections typically utilized for the treatment of neoplasia and prolapse. Although these surgeries may alter the size and shape of the vagina and labia, they may often compromise sexual function or create less than optimal aesthetic results.

Presently utilized surgeries injure tissue, deform anatomy, or remove vital tissue. The sexual dysfunction created by such surgeries may be secondary to stenosis of the vagina, shortening of the vagina, injury to muscles or nerves leading to pain or anesthesia, injury of the Graffenberg Spot, removal of the Graffenberg spot, or poor aesthetic appearance leading to psychological sexual dysfunction.

Injuries to the supporting structures of the vagina and surrounding tissues may also cause urinary incontinence. Present treatments for urinary incontinence do not restore normal anatomic structure. Such treatments either create new support with donor or synthetic tissue or distort anatomy to create a compensatory mechanism for managing the defect. The present invention provides for methods that may be used to change the size or shape of pelvic tissues, wherein such methods may be used for aesthetic procedures, treatments for urinary incontinence, and the like.

BRIEF SUMMARY OF THE INVENTION

In accordance with one embodiment, a method for reshaping pelvic treatment tissue, wherein the method comprises the steps of incising a first tissue layer, removing at least a portion of the first tissue layer, and applying an energy to an underlying tissue layer for initiating shrinkage of the underlying tissue layer.

Another aspect of the present invention provides for a method for reshaping pelvic tissue via transmucosal energy delivery, wherein the method comprises the steps of providing a probe capable of emitting an energy source from a distal end of the probe, inserting the probe into the pelvic tissue, activating the energy source, translating the distal end of the probe across the pelvic tissue, wherein the distal end of the probe is kept in continuous motion, deactivating the energy source, and removing the distal end of the probe from the pelvic tissue.

An additional aspect of the present invention provides for a method for reshaping tissue, the method comprises the steps of providing a device comprising a cannula needle and a laser fiber coaxially disposed within the cannula needle, wherein the laser fiber may be disposed in a retracted position with a distal end of the laser fiber disposed within the distal tip of the cannula needle and an extended position wherein the distal end of the laser fiber protrudes beyond the distal tip of the cannula needle, advancing the cannula needle into the tissue while the laser fiber is in the retracted position, disposing the laser fiber in the extended position, activating the laser fiber for delivery of laser energy to the tissue, withdrawing the cannula needle along the pathway of the step of advancement providing for delivery of the laser energy along the pathway of the step of advancement, and deactivating the laser fiber.

Accordingly, it is the object of the present invention to provide a method to contour one or more pelvic tissues without leading to loss of function or poor aesthetic results. Additionally, one or more of the embodiments of the present invention may also be used to treat urinary incontinence.

DETAILED DESCRIPTION OF THE INVENTION

The scope and breadth of the present inventive disclosure is applicable across a wide variety of procedures, tissues and anatomical structures. Although the following detailed description contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention.

Figure 1A:
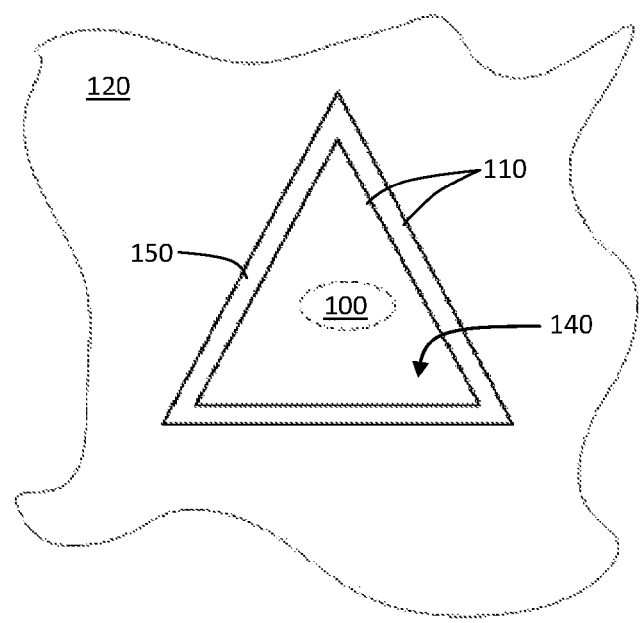
FIG. 1A depicts a schematic diagram of one step in a first embodiment of the present invention.
Figure 1B:
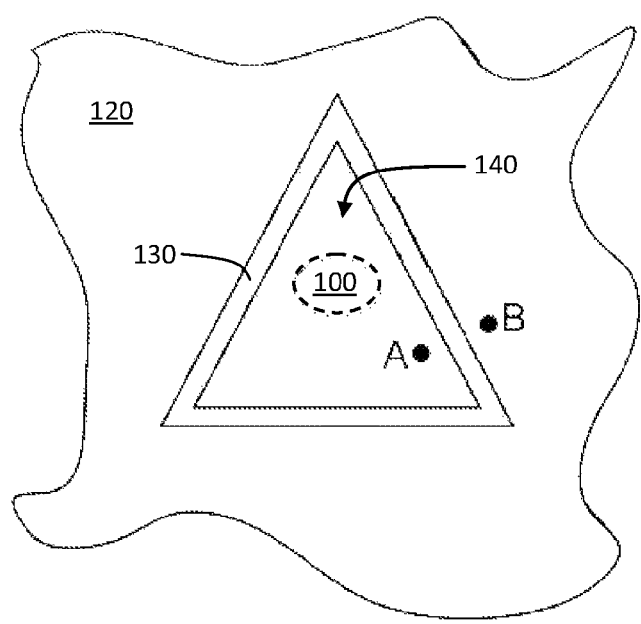
FIG. 1B depicts a schematic diagram of another step in the first embodiment of the present invention.
Figure 1C:
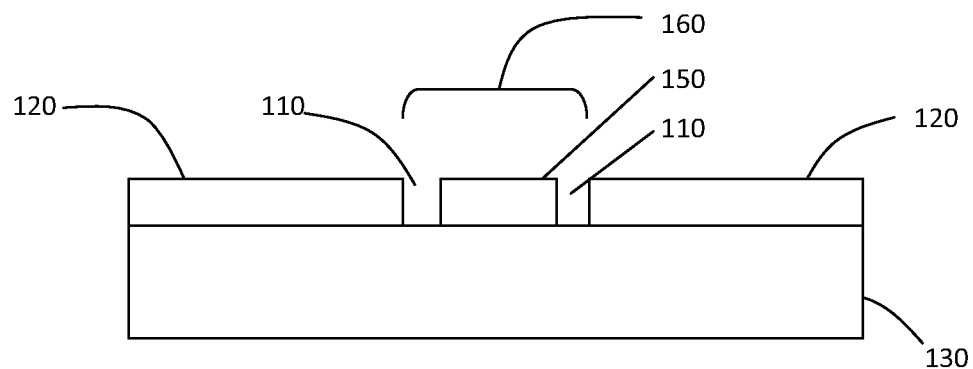
FIG. 1C depicts a schematic diagram of still another step in the first embodiment of the present invention.
Figure 1D:
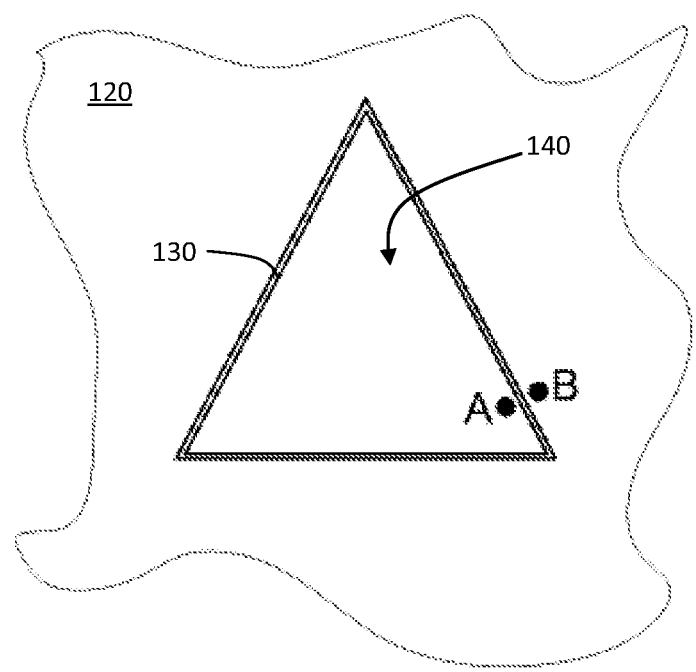
FIG. 1D depicts a schematic diagram of yet another step in the first embodiment of the present invention.

A first embodiment, depicted in FIGS. 1A-1D, may provide for protection of the Graffenberg Spot (G-Spot). In this embodiment, the vaginal mucosa of the G-Spot 100 may be left intact. At least one incision 110 of any known shape, preferably triangular-shaped, may be made around the G-Spot 100, as shown in FIG. 1A. The at least one incision 110 may be carried through the thickness of the vaginal mucosa 120. The at least one incision 110 may spare the endopelvic fascia 130. The at least one incision 110 may assume any known shape thereby defining the shape of an island 140 of tissue. In a preferred embodiment, as shown in FIGS. 1A-1D, a triangular-shaped island 140 of mucosa 120 may be created by the at least one incision 110. A strip 150 of mucosa 120 may be removed from the circumference of the island 140 to expose a channel 160 of endopelvic fascia 130, as shown in FIG. 1B and FIG. 1C. The diameter of this channel 160 will determine the final shape and/or size of the vagina. As shown in FIG. 1D, radio frequency (RF) energy may then be applied to shrink the channel 160 of endopelvic fascia 130 and close the gap between the mucosal 120 edges as shown by the relative movement of point A and point B. The limited penetration of RF energy spares the underlying nerve structure and improves the thickness of peri-island fascia. The mucosal 120 edges may be left "as is", approximated with sutures or glue, or closed by any other manner known within the art. Although RF is the preferred energy source, any other types of energy known within the art including but not limited to laser energy, microwave energy, chemical energy, and monopolar or bipolar electrosurgery may be used.

Figure 2A:
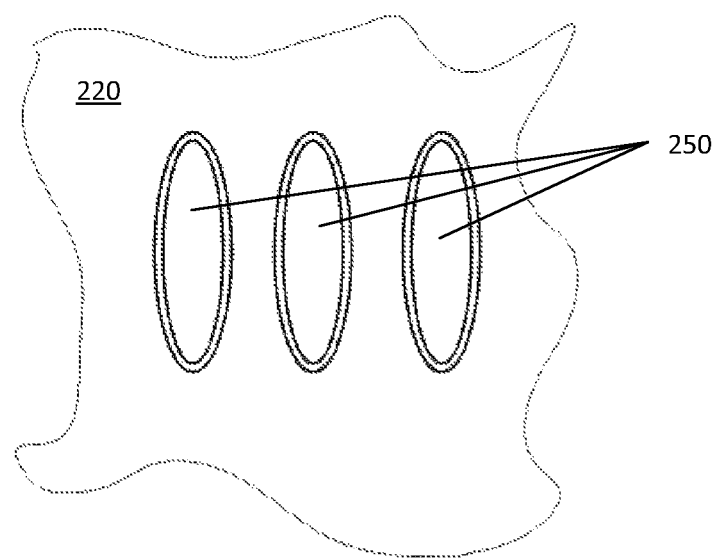
FIG. 2A depicts a schematic diagram of one step in a second embodiment of the present invention.
Figure 2B:
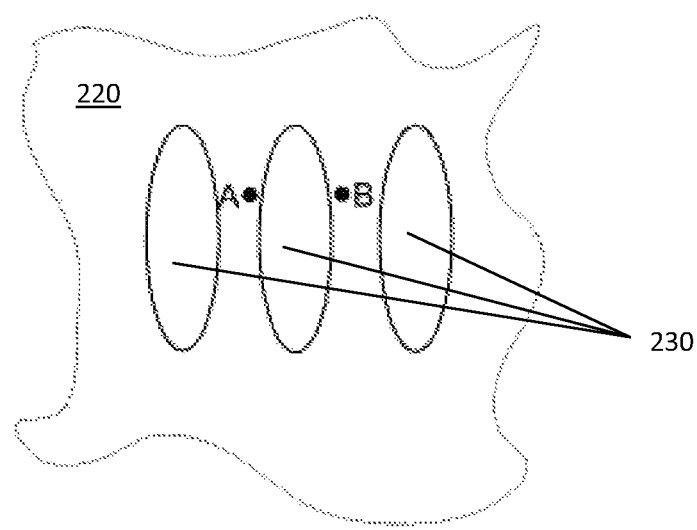
FIG. 2B depicts a schematic diagram of another step in the second embodiment of the present invention.
Figure 2C:
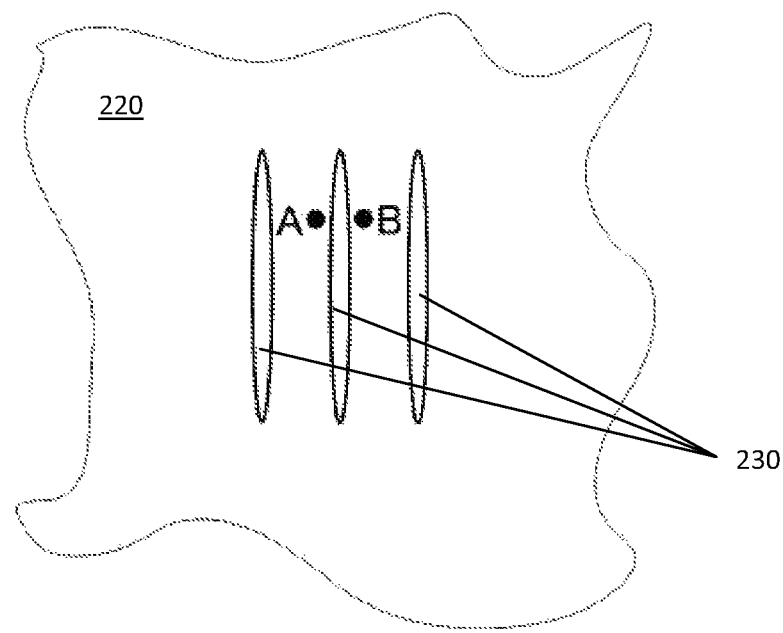
FIG. 2C depicts a schematic diagram of still another step in the second embodiment of the present invention.

A second embodiment, depicted in FIGS. 2A-2C, may provide for vaginal shaping without removal of fascia. In this embodiment, as shown in FIG. 2A, strips 250 of vaginal mucosa layer 220 may be removed while sparing the underlying endopelvic fascia 230 and nerve injury (see FIG. 2B). Rather than pulling the mucosal 220 edges together and creating a submucosal deformity, RF energy may be applied to shrink the endopelvic fascia 230 and bring the mucosal 220 edges closer together, as shown by the relative movement of point A and point B in FIGS. 2B and 2C. The limited penetration of RF energy acts to spare the underlying nerve structure and improves the thickness of underlying tissue. The mucosal 220 edges may be left "as is", approximated with sutures or glue, or closed by any other manner known within the art. Although RF is the preferred energy source, any other types of energy known within the art including but not limited to laser energy, microwave energy, chemical energy, and monopolar or bipolar electrosurgery may be used.

Figure 3A:
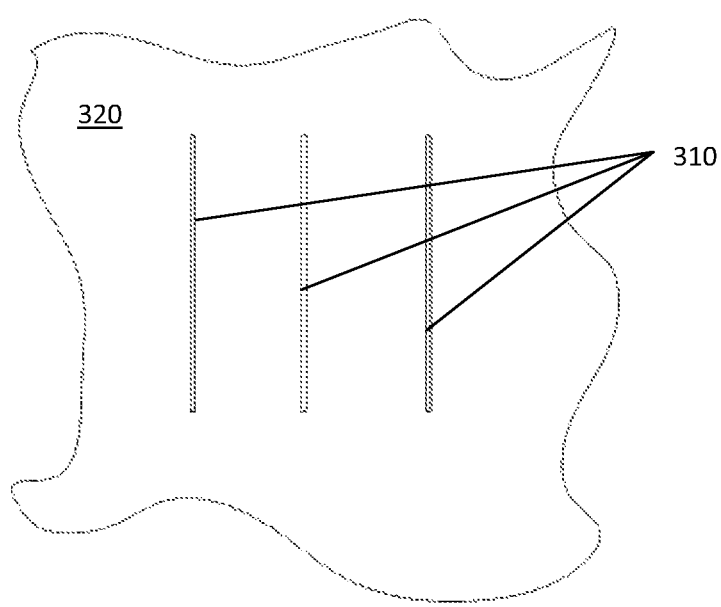
FIG. 3A depicts a schematic diagram of one step in a third embodiment of the present invention.
Figure 3B:
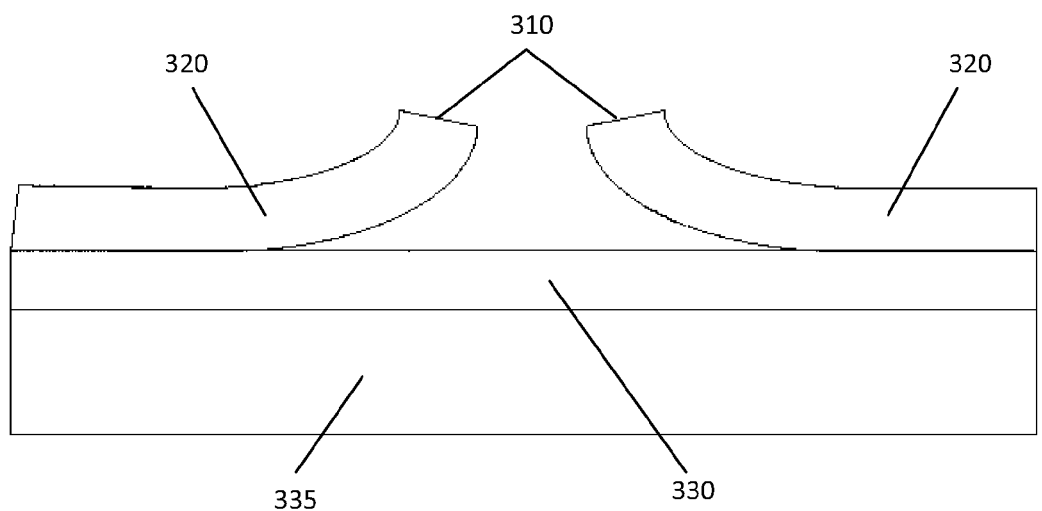
FIG. 3B depicts a schematic diagram of another step in the third embodiment of the present invention.
Figure 3C:
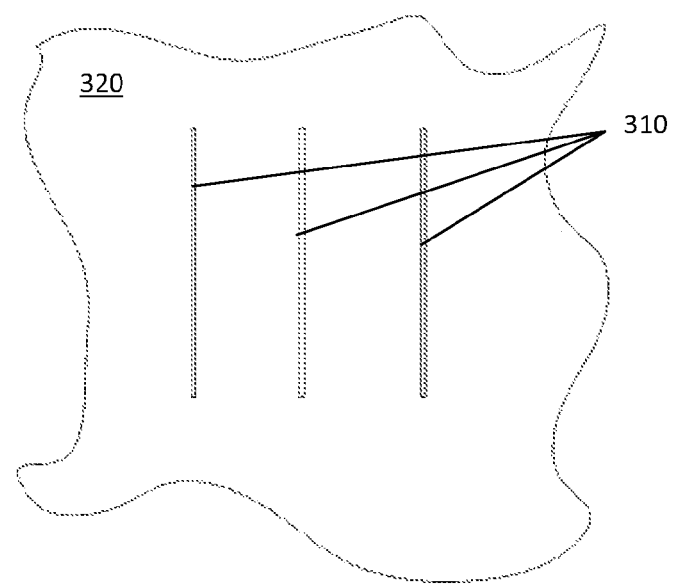
FIG. 3C depicts a schematic diagram of still another step in the third embodiment of the present invention.

A third embodiment, depicted in FIGS. 3A-3C, may provide for vaginal shaping without removal of mucosa. As shown in FIG. 3A, one or more incisions 310 may be made in the mucosa 320. The endopelvic fascia 330 or other submucosal tissue may be left attached to the mucosa 320. As shown in FIG. 3B, RF energy may be applied to the endopelvic fascia 330 or other submucosal tissue exposed between the one or more incision 310 margins. Such an application of energy will cause shrinkage of such endopelvic fascia 330 tissue with proportional contraction of the overlying mucosa 320 and spare the deep nerves and subfascial or subcutaneous tissue 335. Any such endopelvic fascia 330 that is left exposed (as expressly disclosed in all embodiments) may be treated with RF energy. In this manner, the mucosal 320 edges closer together and provide a new contour or shape to the mucosa 320, as shown in FIG. 3C, as the mucosal 320 edges are motivated against each other due to the shrinkage of the endopelvic fascia 330. The mucosal 320 edges may be left "as is", approximated with sutures or glue, or closed by any other manner known within the art. Although RF is the preferred energy source, any other types of energy known within the art including but not limited to laser energy, microwave energy, chemical energy, and monopolar or bipolar electrosurgery may be used.

A fourth embodiment may provide for contouring of the prepuce. As expressly disclosed in the method steps above, one or more incisions may be created around the prepuce and RF energy may thereafter be applied to the underlying fascia. Such an embodiment is similar to that shown in FIGS. 3A-3C and analogous steps may be applied to the prepuce. Although RF is the preferred energy source, any other types of energy known within the art including but not limited to laser energy, microwave energy, chemical energy, and monopolar or bipolar electrosurgery may be used.

A fifth embodiment may provide for contouring of the labia minora. As expressly disclosed in the method steps above, one or more incision may be made in the labia minora. The subcutaneous tissue may not be separated from the epithelium. RF energy may then be applied to the subcutaneous tissue. The shrinkage of the subcutaneous tissue and/or fascia shall contour the labia. Such an embodiment is similar to that shown in FIGS. 3A-3C and analogous steps may be applied to the labia minora. Although RF is the preferred energy source, any other types of energy known within the art including but not limited to laser energy, microwave energy, chemical energy, and monopolar or bipolar electrosurgery may be used.

A sixth embodiment may provide for contouring of the perineum. As expressly disclosed in the method steps above, a portion of perineum skin may be removed sparing the underlying fascia and nerves. RF energy may then be applied to the fascia and other subcutaneous tissue. The shrinkage of the subcutaneous tissue and/or fascia will bring the epithelial edges closer together. The edges may be left "as is", approximated with sutures or glue, or closed by any other manner known within the art. Such an embodiment is similar to that shown in FIGS. 2A-2C and analogous steps may be applied to the perineum. Although RF is the preferred energy source, any other types of energy known within the art including but not limited to laser energy, microwave energy, chemical energy, and monopolar or bipolar electrosurgery may be used.

A seventh embodiment may provide for contouring of the labia majora. As expressly disclosed in the method steps above, one or more incisions may be made in the labia majora. The subcutaneous tissue may not be separated from the epithelium. RF energy may then be applied to the subcutaneous tissue. The shrinkage of the subcutaneous tissue and/or fascia shall contour the labia. Such an embodiment is similar to that shown in FIGS. 3A-3C and analogous steps may be applied to the labia majora. Although RF is the preferred energy source, any other types of energy known within the art including but not limited to laser energy, microwave energy, chemical energy, and monopolar or bipolar electrosurgery may be used.

As an alternative or addition, a portion of labial skin may be removed sparing the underlying fascia and nerves. RF energy may then be applied to the subcutaneous tissue and/or fascia. The shrinkage of the subcutaneous tissue and/or fascia will bring the labial skin edges closer together. The edges may be left "as is", approximated with sutures or glue, or closed by any other manner known within the art. Such an embodiment is similar to that shown in FIGS. 2A-2C and analogous steps may be applied to the labial skin. Although RF is the preferred energy source, any other types of energy known within the art including but not limited to laser energy, microwave energy, chemical energy, and monopolar or bipolar electrosurgery may be used.

Figure 4A:
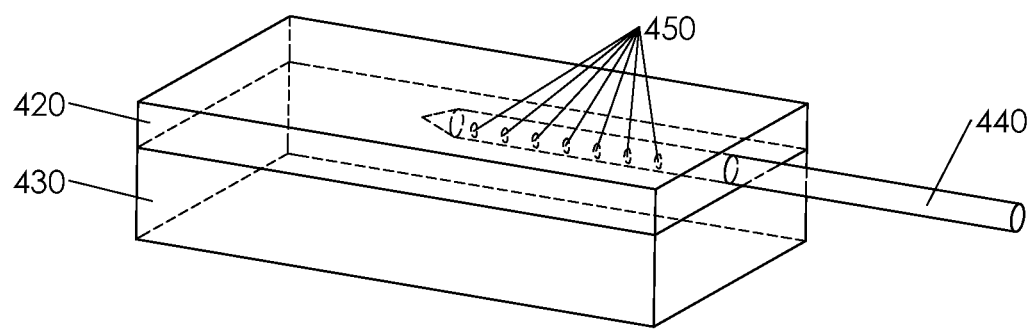
FIG. 4A depicts a schematic diagram of a treatment phase of a fourth embodiment of the present invention.
Figure 4B:
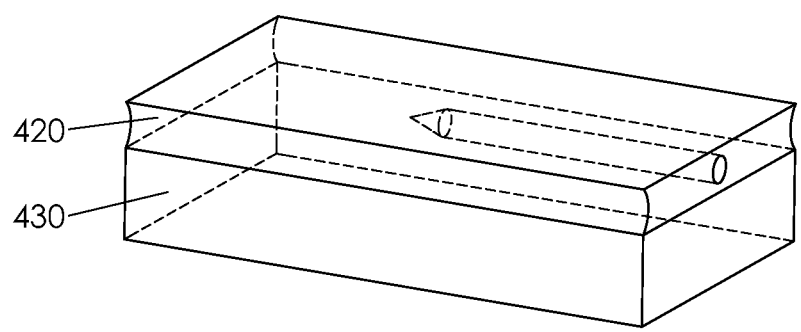
FIG. 4B depicts a schematic diagram of a post-treatment phase of the fourth embodiment of the present invention.

An eighth embodiment, depicted in FIG. 4A and FIG. 4B, may provide for transmucosal and transcutaneous contouring. As shown in FIG. 4A, pelvic tissues including but not limited to the vaginal mucosa, labia, prepuce, and/or perineum may be treated by the transcutaneous application of RF energy. In such an embodiment, RF energy may be applied to the tissue 430 (e.g. dermis, subcutaneous tissue, and/or fascia) below the mucosa or skin 420 without an incision being made or portions of the mucosa or skin 420 being removed. Application of such RF energy may preferably be via a needle, probe, or any other non-invasive instrument 440 known within the art. FIG. 4A depicts one embodiment performing the step of application of energy from one or more side ports 450 of a non-invasive means 440. As shown in FIG. 4B, the resultant shrinkage and changes to underlying tissue 430 shall shape the overlying structures as needed. Although RF is the preferred energy source, any other types of energy known within the art including but not limited to laser energy, microwave energy, chemical energy, and monopolar or bipolar electrosurgery may be used.

Figure 5A:
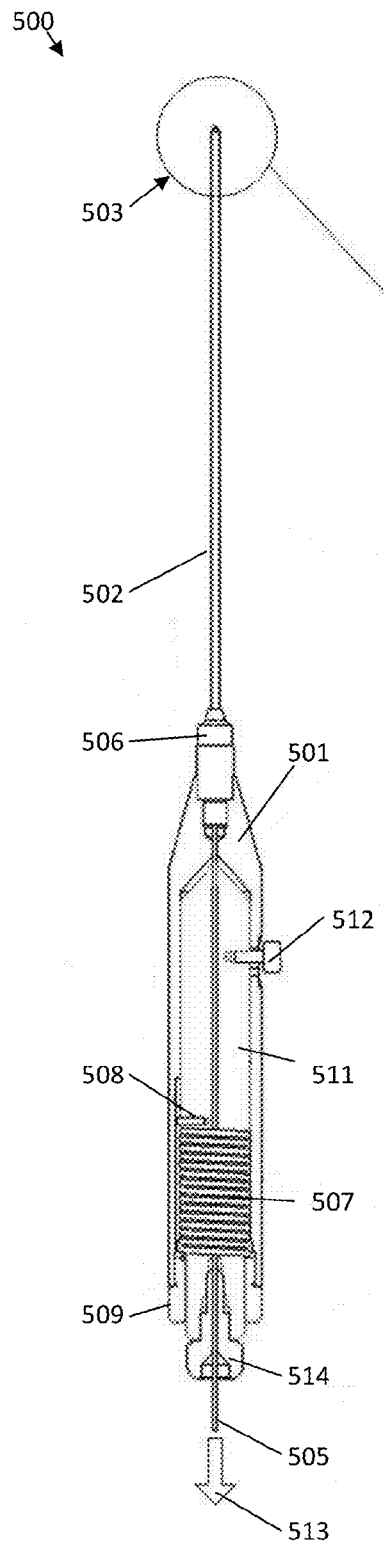
FIG. 5A depicts a side view of one embodiment of a laser energy source of the present invention.
Figure 5B:
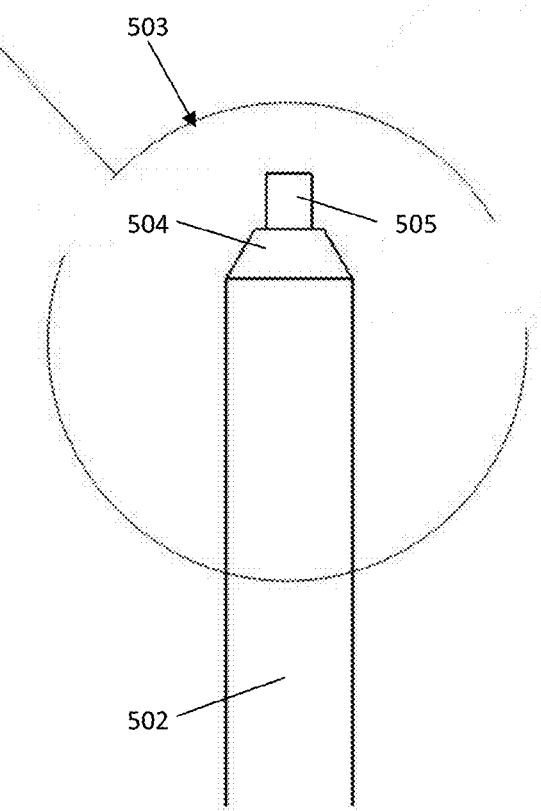
FIG. 5B depicts a magnified side view of the embodiment of the laser energy source of the present invention depicted in FIG. 5A.

Another effective embodiment, similar to that shown in FIGS. 4A and 4B, may involve the use of a cannula needle and laser fiber. FIG. 5A depicts one potential and preferred embodiment of such a cannula needle and laser fiber device 500. In one embodiment, the device 500 may comprise an outer housing 501 secured to a cannula needle 502 having a distal portion 503. The distal portion 503 may comprise a distal tip 504 from which a laser fiber 505 may be extended and retracted. FIG. 5B illustrates a close-up view of the laser fiber 505 disposed in an extended state and protruding beyond the distal tip 504 of the cannula needle 502. The device 500 may comprise additional optional features to facilitate use, such optional features may include but are not limited to male/female Luer locks 506 for attaching the cannula needle to the outer housing 501, and a compression spring 507, clocking pin 508, spring cap 509, slide body 511, and slide limiter 512 providing for modes of extending and retracting the laser fiber 505 relative to the distal tip 504 of the cannula needle 502. The laser fiber 505 may extend from the proximal end of the device 500 to a laser source 513 through a fiber locking screw 514.

In use, the laser fiber 505 may be advanced to the distal portion 503 of the cannula needle 502 without extending beyond the distal tip 504 and thereafter the cannula needle 502 may be inserted through a small puncture and advanced to the desired pelvic treatment area. In one embodiment, the cannula needle 502 may then be slightly retracted disposing the distal end of the laser fiber 505 just beyond the distal tip 504 of the cannula needle 502. The laser fiber 505 may then be activated to deliver laser energy along the path of the cannula needle's 502 withdrawal. This delivery of energy may be supplied either continuously or in a pulsed fashion. The energy being delivered through the distal end of the laser fiber 505 may also be altered in power, pulse width, and/or rest time in order to provide differential treatment along the path of movement of the distal end of the laser fiber 505. Application of energy in this manner may result in a shaping or molding of the tissue rather than a uniform contraction. One example of use of such a device 500 and/or method may be in the vagina where distal application of a greater magnitude of energy will help to create the normal taper of the vagina. In a preferred embodiment, energy may be applied in the form of a 980 nm-1064 nm wavelength laser to be effective. However, other laser wavelengths and other forms of energy may replace a highly preferred 980 nm laser within the scope of the present invention. In a preferred embodiment, 810-1064 nm will be delivered at no less than 4 watts and no more than 25 watts. In the preferred embodiment pulse time will be no less than 0.1 second and no more than 2 seconds continuous energy. However, in circumstances where the cannula needle 502 is kept in continuous motion (pulled out without stopping), the pulse may be equal to the length of time required to treat the entire cannula needle removal or insertion tract with the cannula needle 502 moving no slower than 0.25 cm per second.

In one variation of the preferred embodiment, the energy will be increased or decreased as the distal end of the laser fiber 505 approaches the opening of the vagina. If the vagina needs more tightening near the opening, the energy may be increased at such a location. If the apex of the vagina needs more shrinking relative to the opening of the vagina, the energy will be decreased as the distal end of the laser fiber 505 approaches the vaginal opening. Preferably these power and/or pulse adjustments may be preset in the laser device 500. In one embodiment the laser power and/or pulse width will be serially increased or decreased each time the surgeon deactivates and then reactivates the laser (e.g. releases and steps back down on the laser pedal). Four typical presets may start with the laser power at 12, 14, 17, and 19 watts and increase by 1 watt each time the surgeon reactivates the laser. The maximum increase is typically set between 5 and 10 watts. Once the maximum is reached, there may be no change in power with subsequent activations. Additionally, while the disclosure describes a preferred method of energy application during withdrawal of the device 500, energy may additionally or alternatively be applied or delivered during advancement of the device 500 through the pelvic treatment tissue. Although the present embodiment utilizes a laser as the preferred energy source, any other types of energy known within the art including but not limited to RF energy, microwave energy, chemical energy, and monopolar or bipolar electrosurgery may be used with such respective structures replacing the laser fiber 505.

In a preferred embodiment of the device 500, forward pressure or advancement of the cannula needle 502 may cause the laser fiber 505 to move back against a spring 507. Similarly, backward movement or withdrawal of the cannula needle 502 may cause the laser fiber 505 to be advanced or extended beyond the distal tip 504 of the cannula needle 502 by the biasing force of the spring 507. In an alternate embodiment of the device 500, the laser fiber 505 may require manual advancement against the biasing force of a spring 507 to advance or extend the distal end of the laser fiber 505 beyond the distal tip 504 of the cannula needle 502.

Figure 6A:
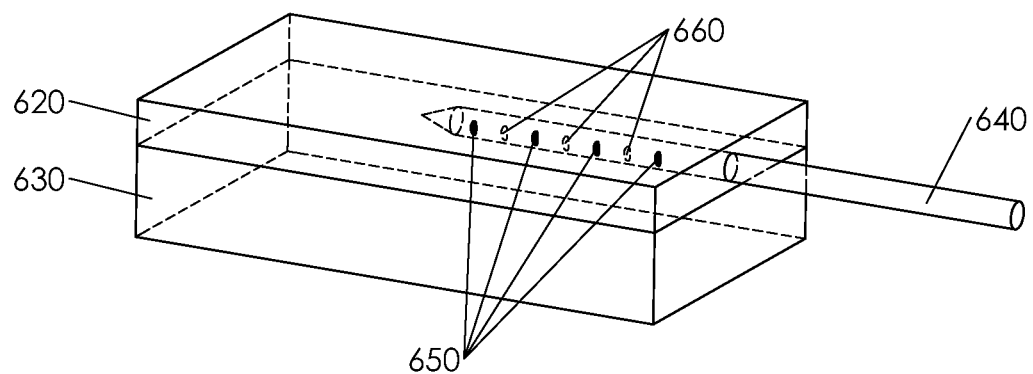
FIG. 6A depicts a schematic diagram of a treatment phase of a fifth embodiment of the present invention.
Figure 6B:
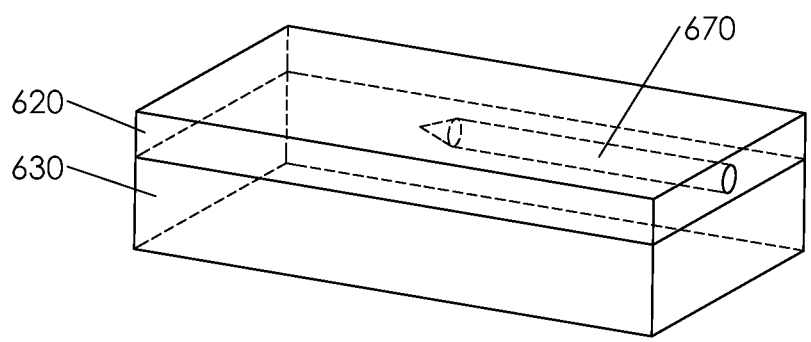
FIG. 6B depicts a schematic diagram of a post-treatment phase of the fifth embodiment of the present invention.

A ninth embodiment, depicted in FIG. 6A and FIG. 6B, may provide for applying minimally destructive energy directly or indirectly to the tissues 620 of the vagina and/or vulva, which may be followed by the implantation of stem cells 670. Such a "pretreatment" of energy may take the form of RF energy, microwave energy, laser energy, chemical energy, monopolar or bipolar electrosurgery, or any other surgical energy sources known within the art. As shown in FIG. 6A, the application of such energy may be delivered with or without an incision. Application of such energy may preferably be via a needle, probe, or any other non-invasive means 640 known within the art having application elements 650 such as ports, conduits, fibers, and the like respective to the specific type of energy source used. The pretreatment of energy creates an environment favorable to stem cells 670. Chemical pretreatment, via any known chemical agent(s), may also provide for minimal destruction and/or minimal injury. As shown in FIG. 6B, following pretreatment with an energy source, stem cells 670 may be implanted within the pelvic treatment tissue through exit ports 660 of the non-invasive instrument 640. Such implantation may be performed with a needle, via an incision, or any other means known within the art. The respective steps of the energy pretreatment and the stem cell implantation treatment may be performed in either one stage or two separate stages and by one device or two separate devices for each step.

A tenth embodiment may provide for a method of treating periurethral tissue. All method steps disclosed herein for decreasing the size or changing the shape of anatomical tissue, most particularly the ninth embodiment above, may further be used in the treatment of periurethral tissue. Such treatments may improve the symptoms commonly associated with urinary incontinence.

Figure 7:
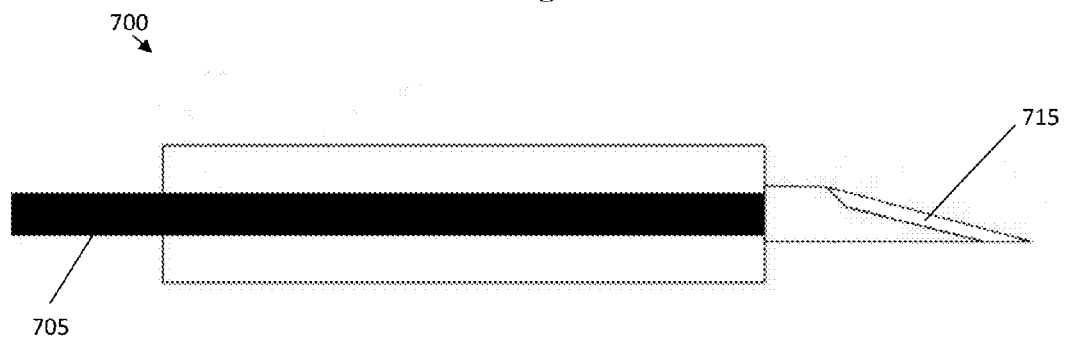
FIG. 7 depicts a side view of another embodiment of a laser energy source of the present invention comprising a laser scalpel.

In an eleventh embodiment, the shaping or resizing of the vulva or other pelvic structure may be facilitated by the delivery of energy through a mechanical cutting instrument. One embodiment of such a device is depicted in FIG. 7 and may consist of a glass scalpel 700 or any other similar instrument known within the art. Such a glass scalpel 700 or equivalent device may be used to create a mechanical cut or incision and simultaneously deliver laser energy for coagulation and tissue treatment (e.g. shrinkage) purposes. In a preferred embodiment, $CO_2$ laser energy may be delivered by a laser fiber 705 to the scalpel cutting blade 715 in the range of 2 watts to 15 watts of continuous power. In a preferred embodiment, the energy will be delivered to the blade as close to $TEM_{00}$ as possible.

Figure 8:
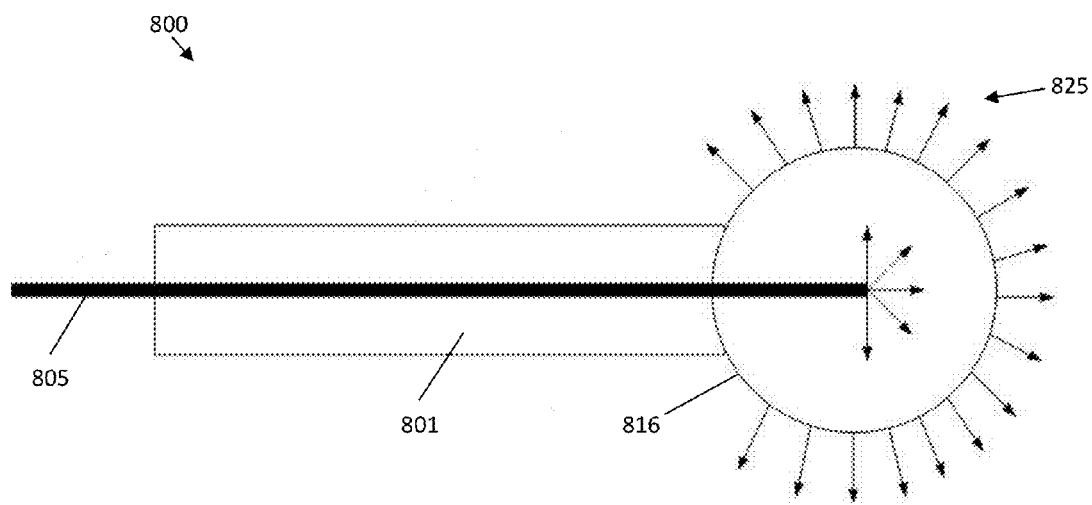
FIG. 8 depicts a side view of another embodiment of a laser energy source of the present invention.

In a twelfth embodiment, as generally depicted in FIG. 8, low level laser energy may be delivered transmucosally to the vagina or other pelvic tissue. The use of such energy has been shown to increase cytochrome c oxidase production and reverse the effects of cellular inhibitors of respiration. Such steps may lead to healing of tissue, reshaping of tissue, and creation of a fertile environment for the potential implantation of stem cells. In one embodiment, the low level laser energy may be delivered via a device 800 comprising a laser fiber 805 disposed inside a vaginal probe 801. The probe 801 may be moved in and out of the vagina in order to deliver the energy to the appropriate surrounding tissues. The probe 801 may be made of glass, plastic, or any other material known within the art and may have a bulbous or "roller ball" type distal end 816. Such a "roller ball" structure may allow for the bulb to illuminate 825 in a uniform 360 degree pattern or as close to such a pattern as possible. Multiple treatments may be necessary to achieve the desired effect. While 980 nm and 808 nm wavelength lasers are the preferred energy sources, other wavelengths, other energy sources including but not limited to RF energy, microwave energy, chemical energy, and monopolar or bipolar electrosurgery, and any combinations thereof may be used within the scope of the present invention.

In one method of use, the probe 801 may be inserted into the vagina until the distal end 816 reaches the vaginal apex. The laser fiber 805 may be in standby mode until the distal end 816 of the probe 801 is at least introduced into the vagina. Once the distal end 816 reaches the apex of the vagina, the laser fiber 805 may be put in ready mode. Once in ready mode, the laser 805 may be activated by stepping on a foot pedal. The user may step on the foot pedal once the distal tip 816 reaches the vaginal apex and then stay on the foot pedal while moving the probe 801 and distal end 816 in an "in and out" motion. In one embodiment, the probe 801 may be kept in constant motion for at least five minutes and reaches a total output of approximately 4200 J. The user may then release the foot pedal to place the laser 805 back in standby mode prior to the extraction of the probe 801 and distal end 816 from the vagina.

While the above description contains much specificity, these should not be construed as limitations on the scope of any embodiment, but as exemplifications of the presently preferred embodiments thereof. Many other ramifications and variations are possible within the teachings of the various embodiments.

Thus the scope of the invention should be determined by the appended claims and their legal equivalents, and not by the specific examples given.

What is claimed is:

1. A method for reshaping pelvic tissue via transmucosal energy delivery, said method comprising:
   the first step of providing a bulbous-tipped laser fiber probe capable of emitting laser energy from a bulbous-tipped distal end of said probe;
   followed by the second step of inserting said probe into said pelvic tissue;
   followed by the third step of activating said laser energy and transmitting said laser energy through said bulbous-tipped distal end of said probe in a bulbous pattern;
   followed by the fourth step of translating said bulbous-tipped distal end of said probe across said pelvic tissue;
   followed by the fifth step of deactivating said laser energy and removing said bulbous-tipped distal end of said probe from said pelvic tissue.

2. The method of claim 1, wherein said laser energy comprises laser energy providing a wavelength in the range from 808 nm to 980 nm.

3. The method of claim 2, wherein said pelvic tissue is further defined as a vagina.

4. The method of claim 3, wherein said second step of inserting said probe into said vagina is further defined as inserting said probe into said vagina until said bulbous-tipped distal end of said probe is positioned at the vaginal apex.

5. The method of claim 1, wherein said fourth step of translating is further defined as moving said bulbous-tipped probe in a distal and proximal motion relative to the site of said second step of insertion.

6. The method of claim 1, wherein said fourth step of translating comprises a time span of at least five minutes.

7. The method of claim 3, wherein said fourth step of translating comprises a time span of at least five minutes.

8. The method of claim 3, wherein said fourth step of translating is further defined as moving said bulbous-tipped probe in a distal and proximal motion relative to the site of said second step of insertion.

9. The method of claim 8, wherein said fourth step of translating comprises a time span of at least five minutes.

10. The method of claim 4, wherein said fourth step of translating comprises a time span of at least five minutes.

11. The method of claim 4, wherein said fourth step of translating is further defined as moving said bulbous-tipped probe in a distal and proximal motion relative to the site of said second step of insertion.

12. The method of claim 11, wherein said fourth step of translating comprises a time span of at least five minutes.

13. The method of claim 5, wherein said fourth step of translating comprises a time span of at least five minutes.

14. The method of claim 4,
wherein said fourth step of translating is further defined as moving said bulbous-tipped probe in a distal and proximal motion relative to the site of said second step of insertion.

15. The method of claim 14, wherein the total laser output is 4200 joules.

16. The method of claim 14, wherein the step of translating comprises a time span of at least five minutes.

17. The method of claim 15, wherein the step of translating comprises a time span of at least five minutes.

\* \* \* \* \*